United States Patent
Besling

(10) Patent No.: US 9,737,245 B2
(45) Date of Patent: Aug. 22, 2017

(54) FLEXIBLE EYE INSERT AND GLUCOSE MEASURING SYSTEM

(75) Inventor: Willem Frederik Adrianus Besling, Eindhoven (NL)

(73) Assignee: NXP B.V., Eindhoven (NL)

( * ) Notice: Subject to any disclaimer, the term of this patent is extended or adjusted under 35 U.S.C. 154(b) by 1198 days.

(21) Appl. No.: 13/435,465

(22) Filed: Mar. 30, 2012

(65) Prior Publication Data

US 2012/0259188 A1  Oct. 11, 2012

(30) Foreign Application Priority Data

Apr. 8, 2011  (EP) .................................... 11161728

(51) Int. Cl.
    *A61B 5/1455*  (2006.01)
    *A61B 5/145*  (2006.01)
    (Continued)

(52) U.S. Cl.
    CPC ........ *A61B 5/14532* (2013.01); *A61B 5/1455* (2013.01); *A61B 5/14507* (2013.01);
    (Continued)

(58) Field of Classification Search
    CPC . A61B 5/0002; A61B 5/1455; A61B 5/14532; A61B 5/14507; A61B 5/6821
    (Continued)

(56) References Cited

U.S. PATENT DOCUMENTS 3,958,560 A    5/1976 March
4,014,321 A *  3/1977 March .......................... 600/319
(Continued)

FOREIGN PATENT DOCUMENTS

| DE | 25 38 985 A1 | 5/1976 |
| GB | 2 365 993 A | 2/2002 |
| WO | 02/03855 A1 | 1/2002 |

OTHER PUBLICATIONS

Badugu, R., et al.; "Boronic Acid Fluorescent Sensors for Monosaccharide Signaling Based on the 6-methoxyquinolinium Heterocyclic Nucleus: Progress Toward Noninvasive and Continuous Glucose Monitoring," Bioorganic & Medicinal Chemistry 13, pp. 113-119 (2005).
(Continued)

Primary Examiner — Eric Winakur
Assistant Examiner — Chu Chuan (JJ) Liu

(57) ABSTRACT

Disclosed is a flexible insert (100) for placement on the human eye, comprising a light source (110) in said insert such that light emitted from the light source is shielded from the human eye upon correct placement of the insert on the human eye, a light-responsive material (120) placed in the light path of the light source, said light-responsive material emitting light upon stimulation by the light from said light source, the intensity of said stimulated emission being sensitive to a chemical interaction of the light-sensitive material with an analyte of interest, a photodetector (130) for detecting the light emitted by the light-responsive material; and a transmitter (140) coupled to the photodetector for transmitting a photodetector reading. The insert may be used in conjunction with a reader for automated monitoring of an analyte of interest such as glucose in the tear fluid of its wearer.

19 Claims, 7 Drawing Sheets

Figure 1:
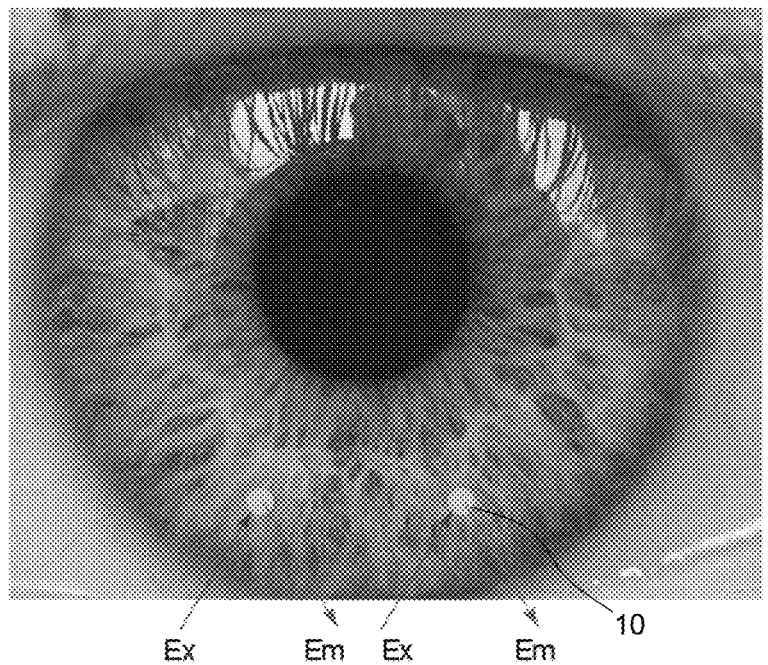

(51) Int. Cl.
*G02C 7/04* (2006.01)
*A61B 5/00* (2006.01)
*A61F 9/00* (2006.01)

(52) U.S. Cl.
CPC .............. *A61B 5/6821* (2013.01); *G02C 7/04* (2013.01); *A61B 5/0002* (2013.01); *A61B 5/0031* (2013.01); *A61B 2560/0219* (2013.01); *A61B 2562/028* (2013.01); *A61B 2562/0233* (2013.01); *A61B 2562/12* (2013.01); *A61F 9/0017* (2013.01)

(58) Field of Classification Search
USPC ....... 600/310, 316, 318, 319, 320, 321, 322, 600/344, 473, 476
See application file for complete search history.

(56) References Cited

U.S. PATENT DOCUMENTS

| | | | |
|---|---|---|---|
| 4,681,412 A | | 7/1987 | Lemelson |
| 4,848,894 A | | 7/1989 | Buser et al. |
| 5,069,214 A | * | 12/1991 | Samaras et al. ............... 600/323 |
| 5,778,878 A | * | 7/1998 | Kellam .......................... 600/310 |
| 6,312,393 B1 | * | 11/2001 | Abreu .......................... 600/558 |
| 2001/0034500 A1 | | 10/2001 | March |
| 2002/0126565 A1 | * | 9/2002 | Kawai et al. ................. 365/233 |
| 2010/0056880 A1 | * | 3/2010 | Cho et al. ...................... 600/301 |

OTHER PUBLICATIONS

Badugu, R., et al.; "A Glucose-Sensing Contact Lens: From Bench Top to Patient", Current Opinion in Biotechnology 2005, vol. 16, pp 100-107 (2005).

Pan, L., et al.; "Self-Monitoring of Blood Glucose Among Adults with Diabetes—United States, 1997-2006"; MMRW Weekly, CDC, vol. 56, No. 43, 6 pages (Nov. 2, 2007).

March, W.F., et al.; "Ocular Glucose Sensor"; Trans. Amer. Soc. Artifi. Intern. Organs, vol. 28, pp. 232-235 (1982).

Badugu, R., et al.; "A Glucose Sensing Contact Lens: A New Approach to Non-Invasive Continuous Physiological Glucose Monitoring", SPIE, Proc. vol. 5317, Optical Fibers and Sensors for Medical Applications IV, pp. 234-245 (2004).

Extended European Search Report for European patent appln. No. 11161728.8 (dated Jul. 28, 2011).

* cited by examiner

FLEXIBLE EYE INSERT AND GLUCOSE MEASURING SYSTEM

CROSS-REFERENCE TO RELATED APPLICATIONS

This application claims the priority under 35 U.S.C. §119 of European patent application no. 11161728.8, filed on Apr. 8, 2011, the contents of which are incorporated by reference herein.

FIELD OF THE INVENTION

The present invention relates to a flexible insert for placement on the human eye that can be used to determine the concentration of an analyte of interest such as glucose in tear fluid.

The present invention further relates to a glucose monitoring system including such a flexible insert.

BACKGROUND OF THE INVENTION

Diabetes is one of the most common global non-communicable diseases. It is the fourth or fifth leading cause of death in most developed countries and there is substantial evidence that it is epidemic in many developing and newly industrialized nations. Type-2 diabetes constitutes about 85 to 95% of all diabetes in developed countries and accounts for an even higher percentage in developing countries. To date about 200 million people have been diagnosed with diabetes. The disease prevalence is expected to grow excessively in the coming years due to the ageing population and the increasing number of people that are over-weight.

Complications from diabetes, such as coronary artery and peripheral vascular disease, stroke, diabetic neuropathy, amputations, renal failure and blindness are resulting in increasing disability and reduced life expectancy, thus causing spiraling health costs in society. This makes diabetes one of the most challenging health problems of the $21^{st}$ century.

In addition to diabetes, the condition of impaired glucose tolerance (IGT) also constitutes a major public health problem, both because of its association with diabetes incidence and its own association with an increased risk of the development of cardiovascular diseases. IGT is recognized as being a stage in the transition to diabetes. About 350 million people have been diagnosed with IGT. Individuals with IGT are at high risk of progressing to type-2 diabetes, with 70% of IGT suffers expected to develop diabetes.

The aforementioned complications from diabetes are typically exacerbated when the blood glucose levels of diabetes sufferers are outside what is considered to be a healthy or normal range. For this reason, blood glucose of diabetic patients is measured regularly to detect hypo- and hyperglycemia and to monitor treatment in order to maintain such normal glucose levels. Continuous tracking of blood glucose level is important to be able to accurately dose glucose level controlling medication, e.g. insulin and maintain normal physiological levels of glucose in the blood.

The goal of maintaining normal physiological levels of glucose has led to the development of many glucose sensing devices suitable for measuring glucose levels both in vivo and in vitro. Most of these sensors are based on electrochemical principles and employ enzymes for molecular recognition. Glucose oxidase for example is used as a glucose sensitive enzyme layer to measure glucose concentration in most test strips.

Traditional glucose monitoring methods to be performed by the patient typically rely on the patient drawing a drop of blood, e.g. by a finger prick, and applying the drop to a test strip. Such methods have the drawback that they are often perceived as uncomfortable, in particular when several daily readings are required, as this can cause soreness of finger tissue due to repetitive pricking. Such distress can lead to non-compliance of the patient with the required monitoring regime, which increases the risk of the patient suffering undesirable blood glucose values. There is therefore a long-felt need to provide blood glucose measurement systems that are perceived as minimally invasive by the patients.

Medtronic MiniMed has developed a new continuous sensor based on the glucose oxidase reaction. The Guardian RT ("Real Time") received FDA approval in August 2005. The system records as many as 864 glucose readings during a three-day period, after which the sensor is replaced. The sensor wirelessly transmits readings to a monitor every 5 minutes. The patient reads the glucose value on the monitor's screen and decides on an insulin dose. Patients can set alarms to warn them of dangerously high or low levels, and all the information can be downloaded to a computer and displayed as reports and charts. The system needs to be calibrated twice a day using a standard blood glucose meter.

Abbott Laboratories, which acquired TheraSense and its FreeStyle product line in 2004, is developing the FreeStyle™ Navigator. This system consists of a biochemical sensor that is inserted under the skin, a transmitter that snaps onto the sensor, and a pager-sized receiver. Information is transmitted wirelessly once every minute. The display shows glucose readings, arrows indicating the trend in the readings, and the rate of change in the trend. The FDA is currently considering pre-market approval for the product in the US.

The DexCom corporation is developing the STS Sensor, which also consists of a sensor inserted under the skin, a wireless transmitter, and a receiver that displays continuous glucose readings and trend information. It also has high and low alerts. The sensor will need to be replaced every three days. The system is currently also under FDA review.

Another approach to a minimally invasive method brings the interstitial fluids out of the tissue so that it can be tested. A technique called reverse iontophoresis applies a weak electrical current to the skin, and pulls interstitial fluids out through the skin and into a measuring device. The Cygnus GlucoWatch G2™ Biographer, which was introduced in 2001, uses this method. The device must be calibrated with a standard blood glucose meter when the sensor is changed, which is every 13 hours.

The SpectRx company is developing a technology that uses a laser to create microscopic holes through the outer layer of dead skin. The interstitial fluid then flows out of the holes into a patch that contains a standard glucose sensor. The results are displayed on a wireless meter.

An alternative approach to measure glucose levels in the interstitial fluids uses microdialysis to extract the interstitial fluids from the skin. A thin catheter is inserted into the subcutaneous fatty layer under the skin. A perfusion fluid inside the catheter is in continuous contact with the interstitial fluid, and pulls glucose into the catheter. The perfusion fluid is then pumped out into a measuring device.

Yet another approach relies on the fact that glucose either absorbs or scatters (near-) infrared light differently than other constituents of the skin and subcutaneous tissue, such that measuring e.g. the scattering effect of a beam of IR projected onto the skin could be used to calculate blood glucose levels.

A different kind of light, fluorescence, may also provide a means of glucose detection and measurement. GluMetrics is another US based company that has developed a glucose sensing technology called GluGlow™. This technology relies on boronic-acid based compounds that glow in the presence of glucose. The company's first application has been announced to be a catheter tipped with GluGlow, that can be used to monitor hospitalized patients.

The university of Maryland has developed a glucose sensing contact lens, which contains boronic acid-based fluoroprobes that exhibit a reduction in their fluorescence intensity upon the covalent binding of D-glucose:

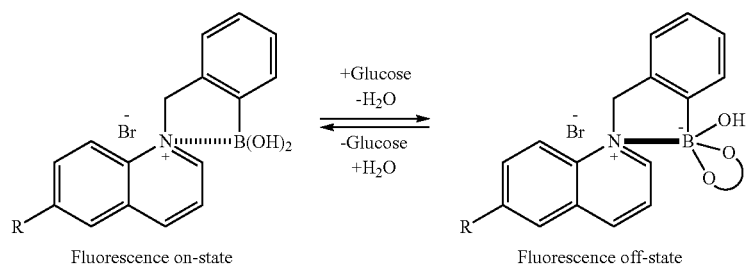

Fluorescence on-state          Fluorescence off-state

An example of such a lens has been disclosed by R. Badugu et al. in Current Opinion in Biotechnology, 16, 2005, pages 100-107. It was reported that the presence of the boronic acid group on the ortho, meta or para-position of the phenyl group bound to the nitrogen made it possible to accurately determine glucose levels in tear fluid by a reduction of the fluorescence intensity from these molecules due to changes in their electron distribution that were induced by the binding of the glucose. It is known per se that the glucose levels in tear fluid reliably follow blood glucose levels with a time lag of approximately 30 minutes. However, a drawback of this lens is that it requires a light source to be directed at the lens when placed in the eye of the patient, which can be perceived as uncomfortable. Moreover, it requires active participation from the patient to monitor glucose levels, which therefore does not avoid the risk of non-compliance with the required monitoring regime.

SUMMARY OF THE INVENTION

The present invention seeks to provide a flexible insert for placement on a human eye that overcomes at least some of the aforementioned drawbacks.

The present invention further seeks to provide a glucose monitoring system including such an insert.

In accordance with an aspect of the present invention, there is provided a insert for placement on the human eye, comprising a light source in said insert such that light emitted from the light source is shielded from the human eye upon correct placement of the insert on the human eye; a light-responsive material placed in the light path of the light source, said light-responsive material emitting light upon stimulation by the light from said light source, the intensity or wavelength of said stimulated emission being proportional to a chemical interaction of the light-sensitive material with an analyte of interest; a photodetector for detecting the light emitted by the light-responsive material; and a transmitter coupled to the photodetector for transmitting a photodetector reading.

The present invention is based on the realization that the integration of a light source such as a light emitting diode (LED) in combination with a photodetector such as a CMOS or CCD sensor can be used to accurately measure analyte levels such as glucose levels in the tear fluid excreted onto the human eye by measuring changes in the stimulated emission, e.g. fluorescence or phosphorescence, of a light-responsive compound placed in the light path of the light source. More particularly, it has been realized that the light source can be integrated into the insert in such a manner that the light generated by the light source can be largely shielded from the human eye, thereby preventing discomfort to the wearer of the insert. In addition, the presence of a transmitter in communication with the photodetector facilitates periodical monitoring of the levels of the analyte of interest in the tear fluid without requiring user intervention, thus increasing the likelihood of compliance to a desired monitoring regime, e.g. a glucose monitoring regime.

Preferably, the insert is a refractive ophthalmic lens to ensure the appropriate orientation of the insert with respect to the cornea of the eye. However, alternative embodiments such as a flexible filament to be placed underneath the lower eye lid are also feasible.

The insert may comprise a first flexible layer and a second flexible layer, and wherein the light source, the light-responsive material, the photodetector and the transmitter are located between said flexible layers. This has the advantage of ease of manufacture. Alternatively, the light source, the light-responsive material, the photodetector and the transmitter may be molded into a single-layer flexible material forming the insert.

In a preferred embodiment, a reflective or refractive layer is present between the light source and the human eye to prevent light emitted by the light source from entering the human eye. Such a layer may have been formed on a surface of the flexible insert carrying the light source or on an external surface of the light source itself. Alternatively, the insert may comprise an interface between two materials having sufficiently different refractive indices, e.g. the lens material and air or the lens material and an internal layer to achieve the desired internal reflection.

More preferably, the light source is placed between the reflective layer and a further reflective layer opposite the reflective layer. In this arrangement the reflective layers cooperate to form a light guide, which ensures that the light emitted by the light source is substantially collimated, thus further reducing exposure of the wearer of the insert to stray light from the light source.

In another embodiment, the insert comprises an optical fiber optically linking the light source to the light-responsive material. The optical fiber is used to direct the light from the light source to the photodetector via this material. In this arrangement an optimal collimated beam is generated which can be directed parallel to the detector surface.

In another embodiment, a light-sensitive surface of the photodetector is facing the human eye upon correct placement of the insert in the human eye. This reduces exposure of the light-sensitive surface to background illumination from ambient light sources, thereby improving the accuracy of the detection of the stimulated emission from the light-responsive material.

Preferably, the photodetector is placed adjacent to and in the proximity of the light source such that light coupled out of the light source substantially evades said light-sensitive surface, as this further improves said detection accuracy.

This detection accuracy may be further improved by a color filter placed over the light-sensitive surface of the photodetector for filtering out the light emitted by the light source as well as ambient light.

The flexible insert may further comprise a charge storage element for powering the light source, the photodetector and/or the transmitter. Preferably, the flexible insert further comprises an inductive coil and/or antenna in the perimeter of the insert, said coil and/or antenna being coupled to the charge storage element for recharging the charge storage element upon exposure to electromagnetic radiation to increase the operational uptime of the insert.

In an embodiment, the light source is a light emitting diode, the light emitting diode further comprising a calibration circuit for measuring the junction temperature of the light emitting diode and for controlling at least one of the drive current and forward voltage of said light emitting diode in response to said junction temperature measurement. This has the advantage that a highly accurate determination of the analyte of interest is made possible due to the fact that variations in the intensity of the light from the light source, which can introduce uncertainty in the analyte measurement result, are compensated for.

In case the analyte of interest is glucose, the light-responsive material may be a boronic acid according to Formula I:

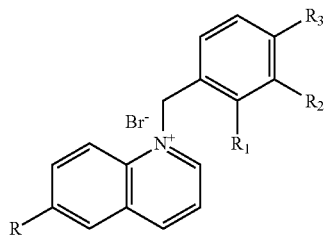

Formula I wherein R is selected from $CH_3$ and $OCH_3$, wherein at most one of $R_1$-$R_3$ is a $B(OH)_2$ group with the remaining groups being hydrogen.

In accordance with another aspect of the present invention, there is provided a glucose-monitoring system comprising the flexible insert of any embodiment of the present invention, as well as a receiver for receiving a signal transmitted by the transmitter of the flexible insert, wherein the receiver is adapted to translate a reading from the photodetector into a glucose level. Such a system allows for automated blood glucose level monitoring such that non-compliance with monitoring regimes, as can be the case in monitoring systems requiring user intervention, is largely avoided.

The glucose-monitoring system may further comprise a holder for the flexible insert, said holder being adapted to recharge the energy storage element of the flexible insert, for instance by the generation of suitable electromagnetic radiation to be picked up by the inductive coil in the flexible insert.

BRIEF DESCRIPTION OF THE EMBODIMENTS

Figure 2:
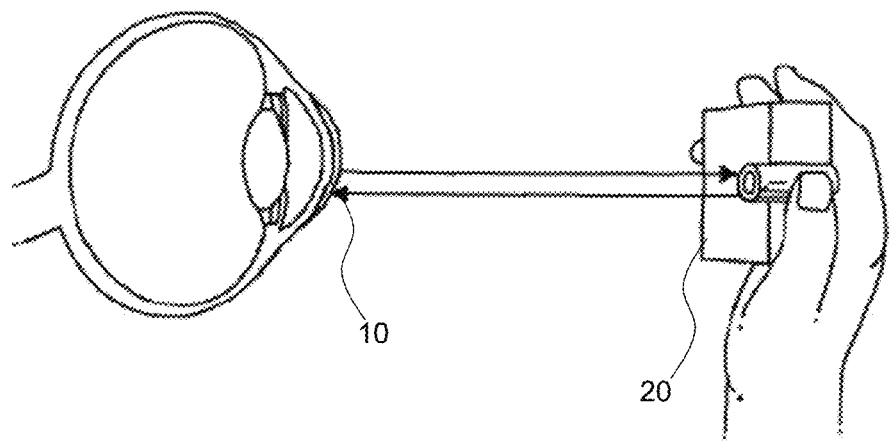
Figure 3:
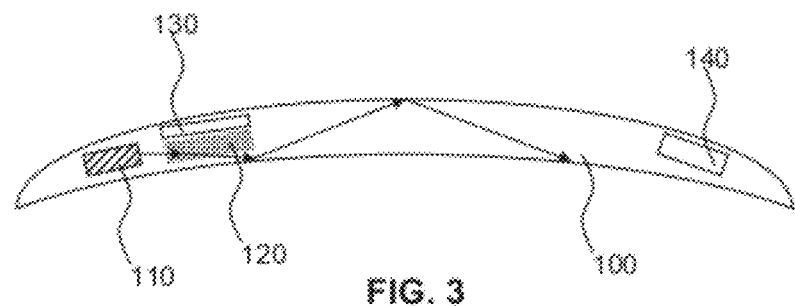
Figure 4:
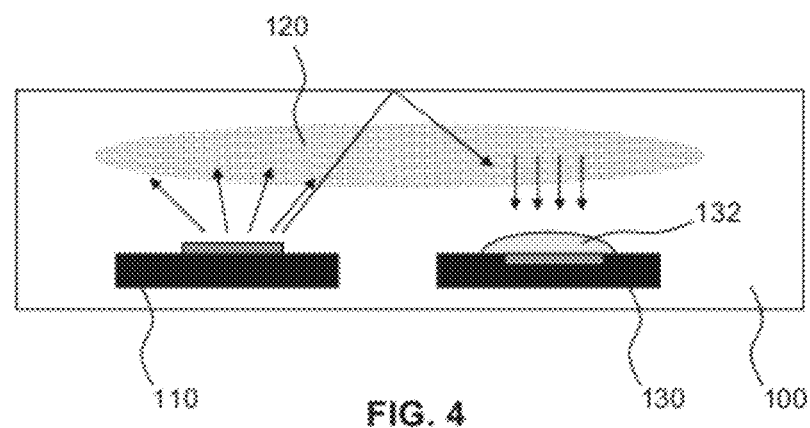
Figure 5:
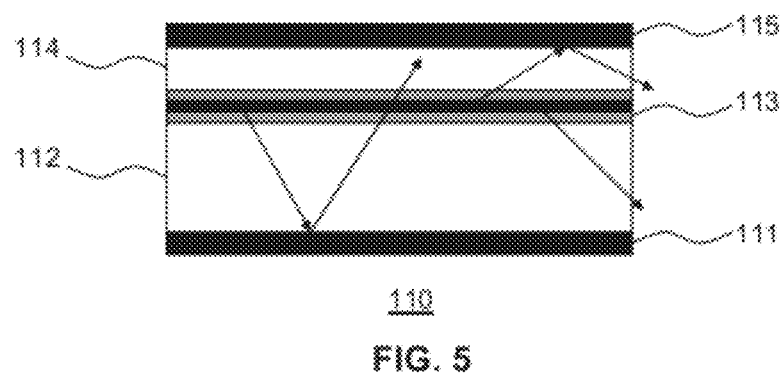
Figure 6A:
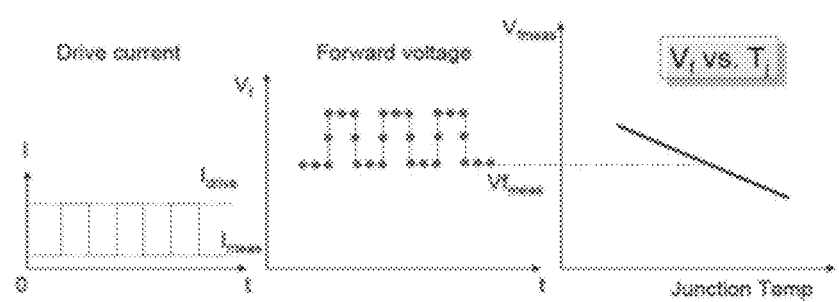
Figure 6B:
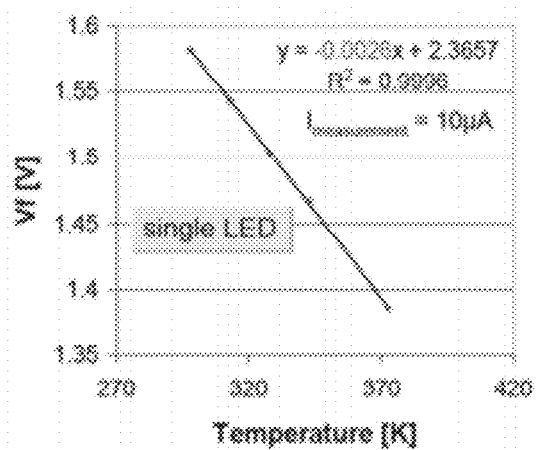
Figure 7:
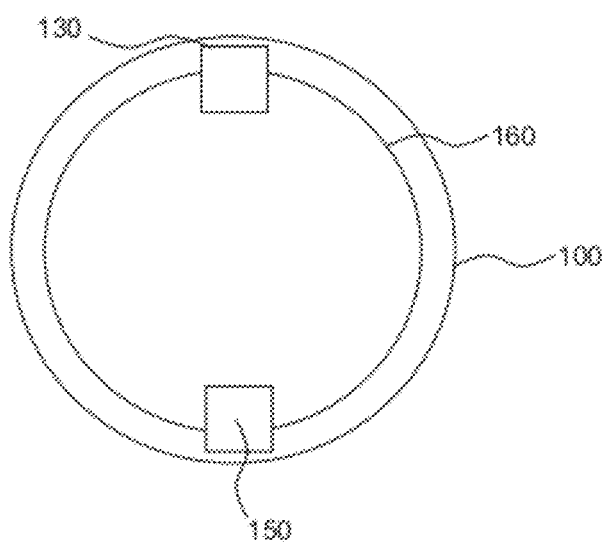
Figure 8:
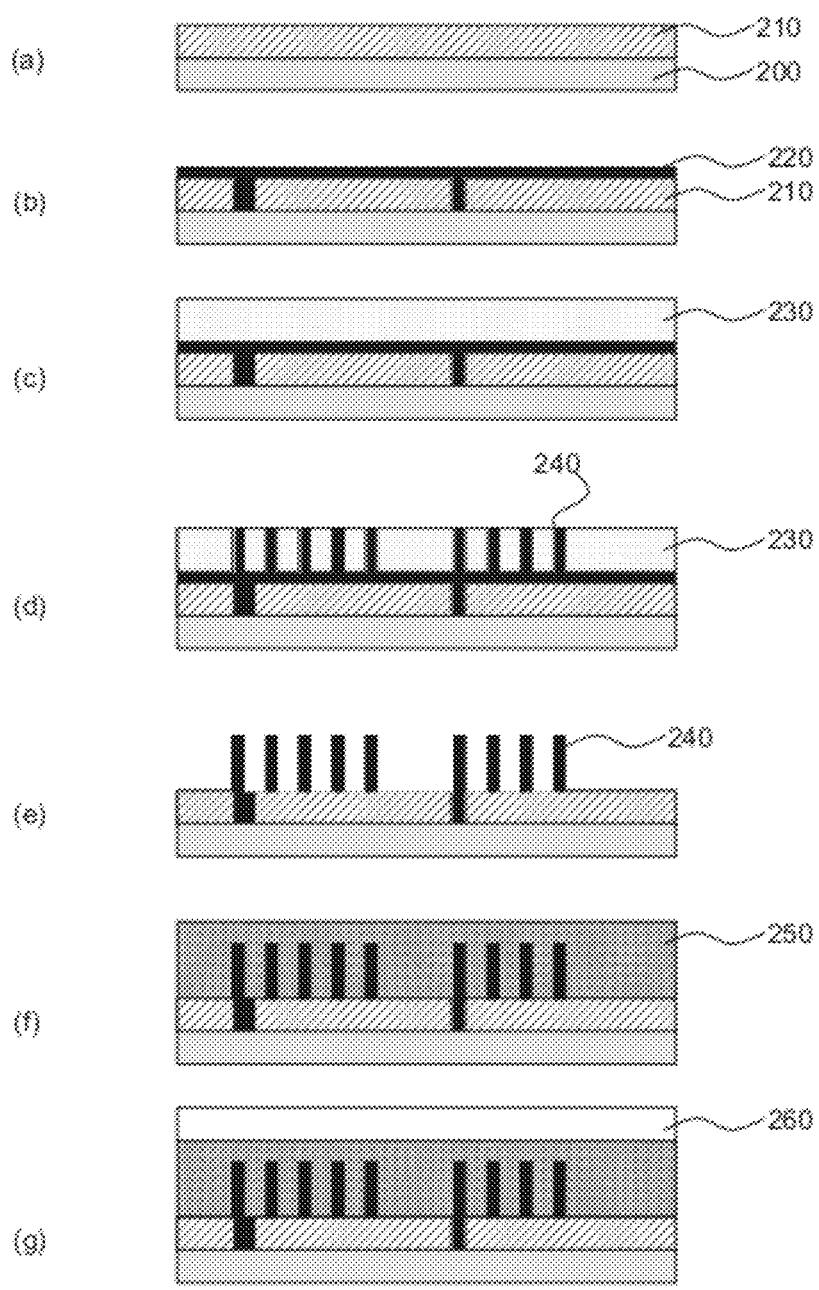
Figure 8:
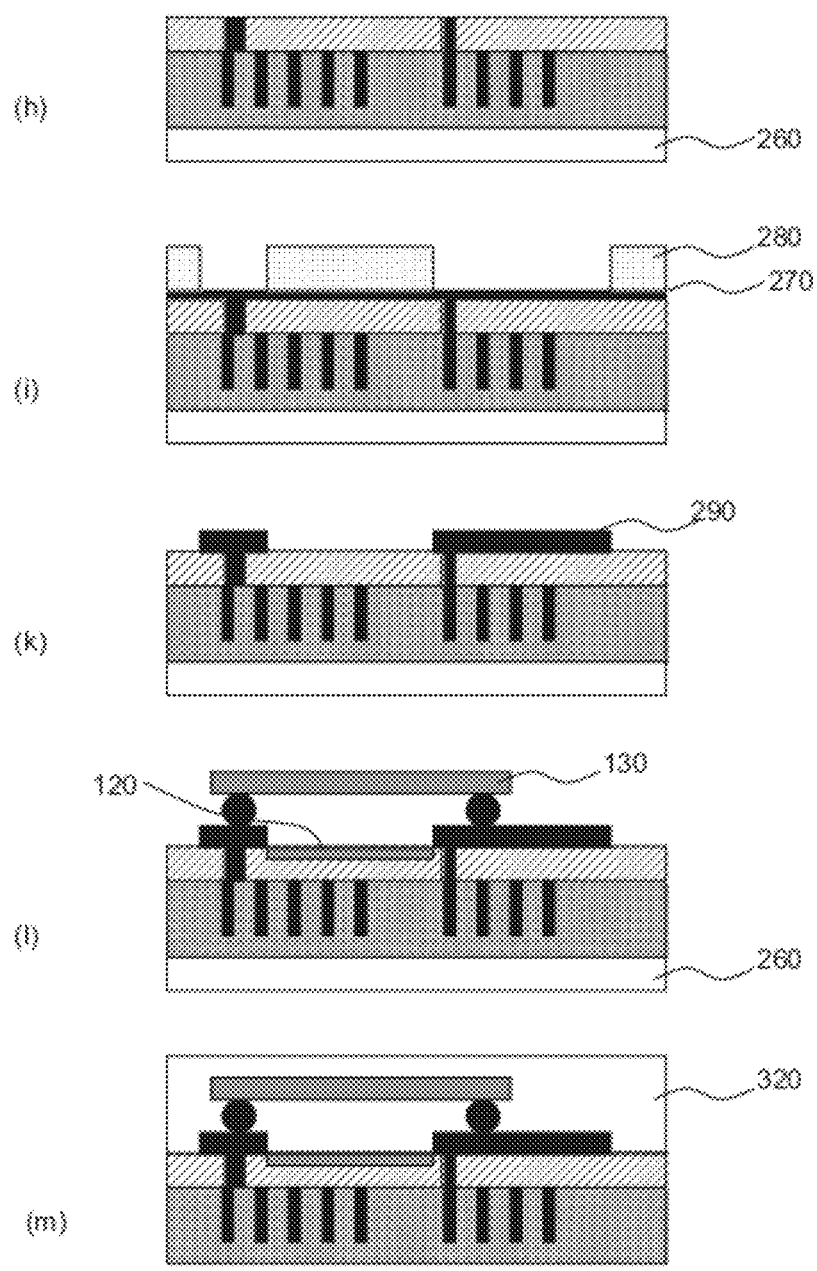
Figure 8:
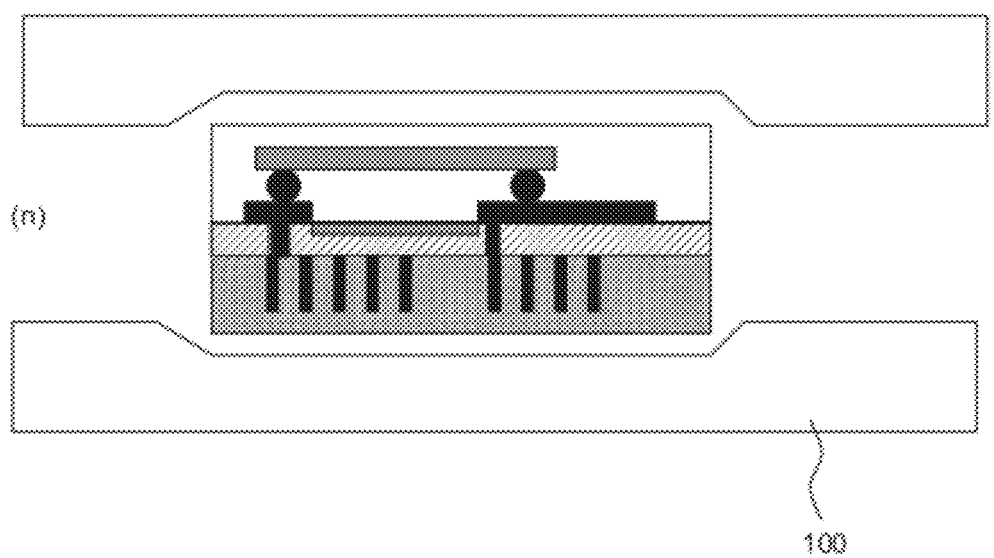

Embodiments of the invention are described in more detail and by way of non-limiting examples with reference to the accompanying drawings, wherein FIG. 1 is an image of a prior art ophthalmic lens inserted in a human eye for detecting glucose levels;

FIG. 2 schematically depicts the read-out mechanism required for the lens in FIG. 1;

FIG. 3 schematically depicts an aspect of an embodiment of an ophthalmic lens of the present invention;

FIG. 4 schematically depicts the detection principle of an embodiment of the ophthalmic lens of the present invention in more detail;

FIG. 5 schematically depicts a light source adapted for use in an embodiment of the ophthalmic lens of the present invention;

FIGS. 6a and 6b depict aspects of a calibration method of a light source for use in the ophthalmic lens of the present invention;

FIG. 7 schematically depicts another aspect of an embodiment of an ophthalmic lens of the present invention; and FIG. 8 depicts an example embodiment of a method of manufacturing an opthalmic lens of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 is an image from the article by Badugu et al. in Current Opinion in Biotechnology, 16, 2005, pages 100-107, in which an ophthalmic lens is disclosed that comprises several sensor spots 10 including a boronic acid-doped sensor spot for detecting glucose levels in the tear fluid in the human eye. As shown in FIG. 2 this article proposes a read-out method in which a separate reader 20 is used to project a flashing light beam onto a sensor spot 10, and measuring the emission intensity of the fluorescence stimulated by the flashing light beam to determine the concentration of an analyte of interest such as glucose present in the tear fluid of the eye into which the ophthalmic lens has been inserted.

A number of boronic acid compounds have been disclosed in this article as being suitable for glucose detection, which share the following Formula I:

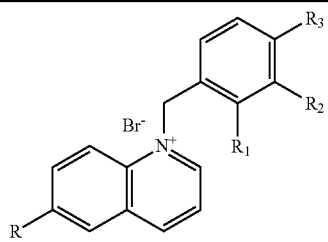

| Compound | R | $R_1$ | $R_2$ | $R_3$ |
|---|---|---|---|---|
| o-BMQBA | $CH_3$ | $B(OH)_2$ | H | H |
| m-BMQBA | $CH_3$ | H | $B(OH)_2$ | H |

| | | | | |
|---|---|---|---|---|
| p-BMQBA | CH$_3$ | H | H | B(OH)$_2$ |
| o-BMOQBA | OCH$_3$ | B(OH)$_2$ | H | H |
| m-BMOQBA | OCH$_3$ | H | B(OH)$_2$ | H |
| p-BMOQBA | OCH$_3$ | H | H | B(OH)$_2$ |

It has been demonstrated in this paper that the B(OH)$_2$-monosubstituted quinolinium bromides have a markedly increased fluorescence intensity sensitivity to glucose binding compared to the quinolinium bromides in which $R_1$-$R_3$=H. This paves the way for the provision of ophthalmic lenses that are doped with such B(OH)$_2$-monosubstituted quinolinium bromides for glucose monitoring. As the glucose-binding reaction of these compounds is fully reversible, this makes them particularly suitable for multiple-use glucose sensing. In addition, these molecules have a relative large Stokes shift of about 100 nm which makes them very interesting for sensor application. Moreover the pKa of these quinolinium based boronic acids can be tuned to the slightly acid nature of the hydrophylic contact lens (pKa=6). Other boronic acids reported in literature also bind 1-2 diols and 1-3 diols selectively thereby increasing the fluorescence intensity but only in alkaline media. The interaction of the quaternary nitrogen center and the boronic acid group not only reduces the pKa but also stabilizes the boronate diester upon complexation with glucose increasing the affinity and selectivity to glucose binding. This is preferable as the glucose level in tears is typically 10× lower (~500 μM) than in blood.

However, the main drawback of the readout principle depicted in FIG. 2 is that the use of an external reading device still requires user intervention, which therefore still suffers the problem that compliance with monitoring regimes becomes a matter of user discipline. In addition, the projection of a flashing light source onto the ophthalmic lens to facilitate a glucose reading can be perceived as uncomfortable, and may even contain health risks such as temporary blind spots in the (peripheral) vision due to the light source or increased risk of an attack for epilepsy sufferers.

The present invention has addressed these problems by the provision of an ophthalmic lens 100 as shown in FIG. 3. The ophthalmic lens 100 comprises, in addition to a light-responsive material 120 such as the compounds of Formula I, a light source 110 for illuminating the light-responsive material 120 with light of a wavelength suitable for triggering the emission of light from the light-responsive material 120. This process is sometimes referred to as stimulated emission and is based on the fact that the light of suitable wavelength brings the responsive material 120 into an electronically excited state, wherein the relaxation back to its electronic ground state takes (at least partially) place via fluorescent pathway (in case of a spin-allowed electronic transition) or phosphorescent pathway (in case of a spin-forbidden electronic transition). In case of the light-responsive material 120 being a boronic acid according to Formula I, blue light, i.e. light having a wavelength of around 400-450 nm, is suitable for bringing the light-responsive material 120 in the electronically excited state from which the fluorescence occurs.

The ophthalmic lens may be made of any suitable material, such as a silicone hydrogel. Silicone hydrogels are known to be suitable lens materials and are permeable to tear fluid, such that the glucose present in the tear fluid can reach the light-responsive material 120 in the lens 100.

A photodetector 130 such as a photodiode is located opposite the light-responsive material 120 to detect and quantify the stimulated emission from the light-responsive material 120. Any suitable type of photodetector may be used for this purpose. Preferably, the photo-sensitive area of the photodetector 130 is directed towards the cornea of the wearer of the ophthalmic lens 100 to minimize the exposure of the photodetector to ambient light, i.e. light originating from outside the ophthalmic lens 100. A transmitter 140, which may take any suitable form, such as a transducer or a transponder operating wirelessly at a suitable frequency, e.g. radiofrequency (RF), is also present in the ophthalmic lens 100, and is in communicative contact with the photodetector 130 for transmitting the readings from the photodetector 130 to a remote receiver (not shown), which may take any suitable form such as a wrist watch or a device connected to the Internet for forwarding the readings to a remote monitoring service.

Although the transmitter 140 is depicted as a separate element in the ophthalmic lens 100, it should be understood that the transmitter 140 and the photodetector 130 may be integrated into a single monolithic device, e.g. a monolithic IC, which may further comprise signal processing circuitry for converting the signal from the photodetector 130 into a digital value that can be transmitted to the receiver. The value may be generated by matching the determined emission intensity with a value of the emission intensity stored in a memory (not shown) as a tuple with a corresponding glucose concentration.

Alternatively, the remote receiver may comprise signal processing circuitry for converting the value received from the transmitter 140 into a glucose reading. As such conversion techniques are known per se, and many alternative embodiments are readily available to the skilled person, this will not be discussed in further detail for the sake of brevity.

The principle of the present invention is depicted in more detail in FIG. 4. The light source 110 is arranged to generate light of a suitable wavelength in the direction of the photoresponsive material 120. A photodetector 130 is located in the ophthalmic lens 100 such that the stimulated emission generated as previously described is at least partially picked up by the photodetector 130. The photodetector 130 preferably should be arranged such that it is not significantly exposed to the light emitted by the light source 110. To this end, the photodetector 130 may be placed in close vicinity to the light source with its photosensitive surface under a close to 90 degree angle with the principal propagation direction of the light generated by the light source 110 such that the light from the light source 110 largely evades the photosensitive surface of the photodetector 130. When measuring at a 90 degree angle, a better signal to noise ratio and lower detection limit can be achieved because only stray light will hit the photodetector surface originating from light scattering inside the opthalmic lens material.

In addition or alternatively thereto, the photodetector 130 may comprise a color filter or grating 132 that filters out the wavelength of the light generated by the light source 110 to further improve the signal-to-noise ratio (SNR) of the signal generated by the photodetector 130. The color filter or grating 132 is transparent to the wavelength of interest, i.e. the wavelength of the stimulated emission from the photoresponsive material 120. The SNR may be further improved by pulsing the light source 110 at a predefined frequency such that the contribution of the light from the light source 110 to the overall signal produced by the photodetector 130 can be filtered out by known correlation techniques, e.g. phase-locking.

In addition or alternatively hereto, the photodetector 130 may comprise of a plurality of sensing elements enabling a ratiometric read-out. The ratiometric approach determines the intensity ratio at two different wavelengths. Hereto, different sensing elements are covered with different color filters or gratings 132 that filter out different wavelengths. This mitigates issues related to fluctuations in fluorescence intensity that could arise due to variations in illumination intensity, and due to variations in manufacturing. The latter could lead to non-uniform fluorophore loading, variation in the optical path length due to small thickness variations in the lens or variation in the positioning of the detection circuit in the lens. The ratiometric read-out allows internal calibration of the signal and could be used to cancel out cross sensitivities to other molecules.

In a preferred embodiment the sensing element is a photodiode and more preferably a light emitting diode. As a photodiode the LED absorbs radiation with a wavelength equal or shorter than the predominant emission wavelength of the LED. If for instance a green LED is used as photodiode emitting at 550 nm all fluorescence emission in blue will be captured but all wavelengths longer than 550 nm will be blocked. If two or more of those photodiodes are stacked on top of each other a color filter can be manufactured that is only sensitive in a relative narrow range. If, for instance, a AlGaN/InGaN/AlGaN multilayer with an emission wavelength of e.g. 450 nm is built on top of a AlGaN/InGaN/AlGaN multilayer with an emission wavelength of e.g. 500 nm two optical detection windows can be created i.e. one for wavelengths below 450 nm and one for wavelengths between 450 nm and 500 nm. The advantage of this approach is the relative sharp wavelength cut off, larger suppression of undesired ambient light detection, and the reduced foot print. AlGaN/InGaN/AlGaN multilayers are preferred candidates for such optical band pass filters as the band gap can be tuned between 1.95 eV and 3.4 eV depending on the In concentration and additional Zn or Mg doping of the InGaN layer. The multilayer with the largest band gap must be constructed on top of the other multilayers in order to filter out the most energetic electromagnetic radiation first.

An other aspect of the invention relates to the determination of the fluorescent decay time. In addition to the fluorescence intensity that increases proportionally to the glucose concentration the fluorescence lifetime is also a measure for the glucose concentration. If the photodiode operation is gated to the pulsed LED excitation current and if the time resolution for each measurement interval is chosen small enough (typically in the order of nanoseconds) the fluorescence intensity can be determined not only during the light pulse but also shortly-thereafter, thus increasing signal to noise ratio. Moreover, a method that relies on fluorescence lifetime measurements is ratiometric and has therefore the intrinsic advantage of not being dependent on the intensity of the incident radiation and/or manufacturing variabilities.

An important aspect of the present invention is that the light source 110, preferably a light-emitting diode, is arranged such that the light generated by the light source 110 exits the light source in the lateral plane of the ophthalmic lens 100. The consequence is that wherever a ray of light generated in the light source 110 encounters the boundary of the ophthalmic lens material, the angle of incidence is such that the ray of light is almost completely internally reflected, as for instance is demonstrated by the arrows in FIG. 3, such that the wearer of the lens is prevented from being exposed to significant amounts of the light generated by the light source 110.

The structure will guide the light output of the LED by total internal reflection when the contact lens material with a high index of refraction, is surrounded by a material with lower permittivity or a lower index of refraction. The critical angle is the angle of incidence above which total internal reflection occurs. The angle of incidence is measured with respect to the normal at the refractive boundary. The critical angle $\theta_c$ is given by:

$$\theta_c = \arcsin\left(\frac{n_2}{n_1}\right)$$

where $n_2$ is the refractive index of the less optically dense medium, and $n_1$ is the refractive index of the more optically dense medium. For a water-air interface this critical angle is 48°27', for a silicone hydrogel-air interface with an index of refraction of 1.42 this angle is 44°76'.

For the case of a relatively rigid transparent insert comprising the light source 110 that is embedded in the flexible polymer matrix of the lens 100 the critical angle (minimum angle for total internal reflection) is determined by the difference in index of refraction between the core and cladding materials of the insert. For a typical interface between hard oxygen permeable insert and a soft e.g. silicone hydrogel based cladding material the angle of internal reflection is 75°.

The internally reflected light has an angle dependent phase shift between the reflected and incident light. This phase shift is polarization dependent and grows as the incidence angle deviates further from the critical angle toward grazing incidence. The polarization of the light is a further means to reduce the amount of incident light from the LED on the photodetector upon applying a polarization filter on the photodiode. If the incident light on the fluorophore molecules is polarized or has become polarized due to internal reflection the emitted fluorescence becomes polarized as well. However, the geometry of the excited molecule results in a different dipole moment than the molecules in their ground state which will alter the polarization direction slightly. In addition, if the excited fluorophore complex is relative mobile and moving and or rotating in space the light will be radiated at different polarization angles during the fluorescent decay. If the fluorophore molecules are attached to a relative stiff membrane the polarization direction can be preserved to some extent. In practice the emitted fluorescence from the fluorophore molecules is depolarized and therefore the polarized stray light can be effectively shielded from the photodetector area.

FIG. 5 depicts a LED 110 having reflective surfaces 111 and 115 such that the light generated by the LED 110 becomes collimated in a lateral direction, i.e. exits the device through the vertical sidewalls. In an example embodiment, the LED 110 comprises an Ag bottom electrode 111 (n-type metallization) acting as a first reflective surface and a Au or an Au/Ni top electrode 115 (p-type metallization) acting as a second reflective surface, in between which the functional layers of the LED 110 are oriented, such as an n-doped GaN contact layer 112, a p-doped GaN contact layer 114, in between which a stack 113 of InGaN/AlGaN/InGaN and/or AlGaN/InGaN/AlGaN as the light emission layer is provided. Such a LED 110 is known to generate blue light that is suitable for the excitation of the photo-responsive material 120 of Formula I.

Alternative arrangements are equally feasible. The LED 110 may for instance comprise additional reflective surfaces to define a (laser) cavity with its opening in the sidewall facing the photo-responsive material 120.

Alternatively, the lower reflective layer 111 and/or the upper reflective layer 115 do not have to be an integral part of the LED 110 but may instead form part of the ophthalmic lens 100. The reflective surface may be deposited directly on the lens material, or on an intermediate substrate in between the lens material and the reflective surface in case of unfavorable adhesion properties between the lens material and the reflective material. The output of the light of the light source 110 is preferably substantially collimated. As a consequence, the placement of a photodetector 130 in close enough vicinity to the light source 110 with its photosensitive surface substantially parallel to the collimation axis ensures that the vast majority of light generated by the light source 110 evades the photodetector 130, thus improving SNR as previously mentioned.

Alternatively, the lower reflective layer 111 and/or the upper reflective layer 115 do not have to be an integral part of the LED 110 or the ophthalmic lens 100 but may instead form part of an optically transparent, rigid insert in the lens 100. The insert comprises the LED 110 and the photodetector 130 and is for instance constructed from poly(methyl methacrylate) (PMMA) (n=1.4914). The advantage of using such an insert is that the optical components can placed much more accurately to each other improving the reproducibility of light collimation, and focusing the light to the desired location. Moreover, the manufacturability could be improved as the insert can be placed/positioned more accurately in the ophthalmic lens during the silicone hydrogel overmoulding process.

In a further alternative embodiment the ophthalmic lens 100 may comprise an optical fiber (not shown) acting as a light guide for guiding and collimating the light generated by the LED 110 onto the photo-responsive material 120.

At this point it is noted that the wavelength and light output of a light source such as a light emitting diode 110 can vary depending on factors such as variation in drive current and forward voltage, but also junction temperature due to heating, and aging. It is preferable to control these factors as variation in light output and wavelength could reduce the stimulated emission yield and therefore have an impact on the concentration reading of the analyte of interest, e.g. glucose.

In order to compensate for such variations, in an embodiment the junction temperature $T_j$ of the LED 110 is monitored using an internal calibration arrangement. The junction temperature is a suitable parameter for monitoring because it affects light flux, $\phi$, wavelength, $\lambda$, and forward voltage, Vf. Calibration may for instance be performed by providing the junction with a very low measurement current and monitoring the Vf response to this measurement current. Non-limiting examples of suitable current and voltage waveforms are shown in FIG. 6a (left and middle pane). The forward voltage Vf is a linear function of the junction temperature, as shown in FIG. 6a (right pane) and FIG. 6b.

In an embodiment, very small measurement currents that typically have intensities much lower than 100 µA, e.g. 10 µA, may be inserted in between the high current pulses of the LED used to generate a pulsed light output. The measurement current pulses are used to derive the junction temperature in a continuous fashion. In response to the determined temperature, the drive current of the LED 110 is adapted to generate a constant light output.

A further aspect of the ophthalmic lens 100 is shown in FIG. 7, which schematically depicts the presence of a rechargeable charge storage device or power supply 150 in the periphery of the lens 100, which is used to power the various electronic components such as the photodetector 130 and the light source and transmitter (not shown in FIG. 7). The ophthalmic lens 100 may further comprise one or more inductive coils or antennae 160 for recharging the power supply 150, and for conductively connecting the various electronic components of the lens 100 to the power supply 150.

The rechargeable power supply 150 acts as a local energy buffer to operate the light source 110, photodetector 130, the microprocessor (not shown) and the transceiver 140. In certain embodiments, the energy demand of these electronic components is too large to be supplied by a solar cell, capacitor, RF power, wireless induction), or magnetic induction. The power supply 150 should have a capacity that is large enough to power a clock, allow measurements being performed and transmit data to a wrist watch during 16-24 hours of operation before requiring recharging. Such recharging may for instance be realized by the provision of a lens container, e.g. a cleaning container that includes an RF source such that the power supply 150, e.g. a battery, can be recharged inductively via one or more coils 160 integrated in the lens 100.

Given the power requirements and the limited volume inside the ophthalmic lens 100, a 3D thin film rechargeable Li-ion battery is particularly suitable as the power supply 100 as such batteries are known to have much higher energy densities per unit volume than available planar thin film batteries that are in the market. This is achieved by using a three-dimensional curved surface as substrate material or as template for the deposition of the battery stack creating a significant surface area enlargement. The 3-D surface enlargement can increase both the capacity and peak power of a 3-D battery with a factor of 10 compared to linear batteries, which is beneficial for applications where a high energetic capacity per unit volume is essential to provide the required operational time, such as the present application.

An additional advantage of such a 3-D battery is that due to the use of the third dimension the battery can be made flexible, which allows the battery to be integrated much more easily in a curved contact lens 100 than a rigid square battery. When the battery substrate is fully rigid the maximum allowed substrate thickness is 50 µm with maximum die size i.e. surface area of 2.5×2.5 mm to be able to integrate the battery inside the polymer shell of the contact lens. If the battery is flexible, its size can be significantly increased without the risk of protrusion of the lens 100.

The power consumption by the electronic components of the ophthalmic lens 100 of the present invention may be further reduced by the application of duty cycling, i.e. periodically switching the electronic components to an active state. The power needed during autonomous operation is the power to operate a clock, a microcontroller, the light source and photodetector for data acquisition, and the transceiver for data transfer. Depending on the desired duty cycle the clock initializes the microprocessor and sensor part of the lens 100 e.g. every minute. If the duty cycle is chosen large enough and power gating is applied during inactive intervals to minimize internal leakage current, the total power consumption will be dominated by the power consumption of the clock.

Therefore, it is advantageous to choose a clock design that is low power. The design restrictions are that the clock must be able to be embedded in the ophthalmic lens 100. These criteria are for instance met by a CMOS based ring oscillator clock, which has the further advantage that it is low cost. Although CMOS ring oscillators have limited accuracy, this is not a concern in the present application domain. Moreover, the clock can be reset when the lens is taken out and the battery is recharged in the contact lens holder. Moreover, as the ophthalmic contact lens 100 is in contact with the human body during wear, temperature drift of the duty cycle will be minimal as the body temperature is more or less constant.

A CMOS ring oscillator can be manufactured at low cost but more importantly can be thinned down to less than 50 μm thickness. In contrast, the size of a quartz oscillator makes the total size of the package too large for application in a contact lens, as the use of quartz crystals can easily increase the thickness of the chip in excess of 400 μm, as such quartz oscillators are typically enclosed in a plastic overmoulded package that is too thick to be embedded in contact lenses. For this reason, CMOS clocks or MEMS based oscillators may be used as they are thin and have a very small footprint. In an alternative embodiment, such clocks or oscillators may be monolithically integrated with the chip, thus further reducing size.

In combination with a 3-D rechargeable cell such as a lithium battery, duty cycling for the sensor operation and transceiver enables the operational periods for the lens 100 up to 24 hours. To this end, a 2.5×2.5 mm battery with a cathode thickness of 5 μm deposited in a 3D trench of 50 μm deep, which has a capacity of 0.15 mWh, may be used as such a battery provides sufficient energy for operation of the lens for a whole day.

Another embodiment uses continuous energy harvesting methods during operation, e.g. utilizing induction principles. This has the advantage that a number of components such as a energy storage element like a battery and on board clock can be omitted which facilitates ease of integration and reduces manufacturing costs. On the other hand flexibility and ease of use is compromised as power needs to be transmitted continuously to the device. The minimum required distance between the reader console that emits the electromagnetic radiation and the device that contains the sensor could become a limiting factor here.

It is preferable to use an appropriate CMOS technology to ensure low power consumption and at the same time be small enough to embed the silicon into the available area inside a lens. In an example embodiment, the required total chip size dimensions are less than 1×1×0.1 mm³, for the chip to be able to fit in a typical curvature of a lens having a radius of around 7.8 mm and having a thickness of approximately 200 μm at the rim. For low power consumption relatively thick gate oxides may be used to minimize leakage current. For instance, a typical 0.14 μm CMOS process gives the best compromise for optimizing power management, performing on board data processing by a microcontroller and storing the measurement data in a memory and delivering the required voltage level to illuminate the LED and sending the data back to the reader.

In order to save power duty cycling may be used for the LED operation and for the transmitter (radio) that sends the measurement data back to the reader. There are multiple options to deliver power to the device in a continuous fashion and charge the energy storage component which can be an on-chip capacitor with sufficient capacity to store the energy between the read-out intervals. Magnetic induction or a RF source can be used to transfer power continuously. Other suitable implementations will be apparent to the skilled reader.

As an example the maximum theoretical distance can be calculated for a 2.4 GHz dipole antenna emitting at 1 W, which is the maximum allowed transmit power in 2.4 GHz band as allowed by FCC regulations, to deliver 2 μW continuous power to the electronic circuitry inside the lens. Already at 2 μW continuous power one could accumulate sufficient energy to operate an ASIC comprising e.g. a microprocessor, on board memory, a photodetector circuit, and a radio, to ignite a 500 μW blue LED once every minute and to send the data back to the reader once every ten minutes. If one measurement consists of a pulse train of ten light pulses of 1 ms long, the total power consumption for the LED amounts to 5 μW per measurement. It should be understood that this is a non-limiting example only, and that other power consumptions, e.g. because of different dimensioning of the electronic circuitry, different pulse characteristics and so on, are equally feasible.

The minimum achievable input power is determined by two constraints: the antenna/rectifier power efficiency, and the amplitude of the input voltage to the rectifier which in turn is constrained by the LED turn-on voltage, rectifier threshold and impedance matching to the antenna. By way of non-limiting example, an antenna efficiency of 3.5% can be derived for a single turn loop antenna integrated in the lens 100 having a typical radius r=5 mm, a wire width w=20 μm, a thickness t=10 μm, conductivity of gold of $\sigma=4.52\times 10^7$ $\Omega^{-1}m^{-1}$ and a carrier frequency f=2.4 GHz.

Assuming a combined, average power consumption of the LED and the electronic circuit of 2 μW and a 5% power conversion efficiency for the rectifier at least 40 μW input power is required for the antenna. Furthermore, the antenna efficiency will drop to 1%-1.5% if a non-ideal orientation of the antenna and absorption effects are taken into account. Therefore, the maximum incident power on the antenna must be at least 3.2 mW (5 dBm) to be able to operate the device. This results in a maximum operating distance of 56 cm which would perfectly fit the user conditions. However, performance could deteriorate due to suboptimal matching, interface reflections, and absorption in the lens material. On the other hand, further optimizations could be made to the antenna adding more windings and increasing the thickness and width of the coil such that it can be derived from the above non-limiting example that the lens 100 is capable of delivering a robust and reliable analyte, e.g. glucose, monitoring solution.

At this point it is noted that the teachings of the present invention are not limited to the detection of glucose as the analyte of interest. As it is known per se that the stimulated emission, e.g. fluorescence of compounds may be altered by for instance pH changes or changes in the chemical composition of fluids including tear fluid, photo-responsive materials that are sensitive to such changes may be included to the lens 100 in addition to or instead of the photo-responsive compound 120 for detecting glucose.

It is furthermore noted that the present invention is not limited to eye inserts that take the shape of an ophthalmic lens 100. It is for instance also feasible to provide a fibrous filament for placement under the lower eyelid in which the aforementioned electronic components have been integrated. Other suitable alternatives will be apparent to the skilled person.

In the following, an example embodiment of a manufacturing process of the ophthalmic lens 100 will be provided. It will be appreciated that since many methods of integrating electronic components onto or into flexible carriers are readily available to the skilled person, it should therefore be understood that the example embodiment shown in FIG. 8 is a non-limiting example only and that alternative embodiments will be readily available to the skilled person.

In step (a) of FIG. 8, the method starts with the provision of a suitable transfer substrate 200 onto which a polymer film 210 is formed in any suitable manner, e.g. by spin-coating. A thermally degradable coating (not shown) may be formed in between the transfer substrate 200 and the polymer film 210 to assist in the release of the transfer substrate 200 from the overall structure at a later stage. The transfer substrate 200 may be any suitable substrate, e.g. a silicon or other semiconductor wafer, a glass plate or a flexible carrier. The polymer film 210 may be any suitable material, e.g. silicone, PMMA or polyimide.

The polymer film 210 is subsequently patterned in any suitable manner, e.g. by selective exposure to actinic radiation followed by a wet development step to develop crossover regions for a coil or antenna to be formed. A seed layer 220 for forming such metal structures is deposited over the resultant structure. This is shown in step (b). Such a seed layer 220 may for instance be formed by the deposition of Ti followed by an Au deposition, e.g. using physical vapor deposition (PVD) techniques. The metal for the adhesion layer is typically Ti from biocompatibility reasons but also TiN, TiC, Ta or TaN films can be applied. The metals used for the coil are preferably noble metals such as Au and Ag that can be electrodeposited. Au is preferred because of its high oxidation resistance, malleability, biocompatibility and standard bonding techniques to electrical circuits.

Next, a resist layer 230 is formed over the resultant structure as shown in step (c). This resist preferably should have a thickness in excess of 10 µm to allow for through-resist plating. The resist is subsequently patterned in any suitable manner, e.g. using UV lithography, to define the regions in which the coil or antenna is to be formed, after which a suitable metal 240, e.g. Au, is electroplated into the exposed regions as shown in step (d) after which the resist 230 and the seed layer 220 are removed, e.g. by stripping and wet etching respectively, to leave the coil or antenna 240 defined on the polymer film 210 as shown in step (e).

The method proceeds as shown in step (f), in which the coil or antenna 240 is subsequently embedded in a polymer isolation layer 250, which may be deposited in any suitable manner, e.g. by spin or spray coating depending on the aspect ratio of the windings of the coil or antenna 240: A further transfer substrate 260 is subsequently deposited over the polymer isolation layer 250. This is shown in step (g). The further transfer substrate 260 may be any suitable material, e.g. a glass substrate. A degradable release coating (not shown) may be formed between the polymer isolation layer 250 and the further transfer substrate 260 to aid in the release of the further transfer substrate 260 from the remainder of the device.

Next, as shown in step (h), the first transfer substrate 200 is released, e.g. by a heat treatment step to decompose the thermally decomposable release layer between the transfer substrate 200 and the polymer film 210, and the remaining wafer is flipped. At this point it is noted that preferably the degradable release coating between the polymer isolation layer 250 and the further transfer substrate 260 is preferably formed of a material that can be degraded by UV exposure such that this material is not affected by the release of the first transfer substrate 200. Alternatively, this material is a thermally degradable material with a decomposition temperature well above the decomposition temperature of the thermally decomposable release layer between the transfer substrate 200 and the polymer film 210.

As shown in step (i), a further seed layer 270 is subsequently formed, e.g. a Ti/Au seed layer 270, a resist 280 is formed over the seed layer 270 and subsequently patterned. The seed layer 270 is to facilitate the formation of the metallic connections of the chip. The resist 280 preferably has a thickness exceeding 10 µm to facilitate through-resist plating as previously explained. The metal connections 290, e.g. Au connections, are subsequently electroplated in the exposed regions of the resultant structure, i.e. those regions where the resist 280 has been removed, after which the resist 280 is removed, e.g. stripped from the resultant structure, followed by the removal of the excess seed layer 270 in any suitable manner, e.g. wet etching. This is shown in step (k).

The method proceeds to step (I) in which a suitable polymer 120 comprising the glucose-sensitive fluorophores is deposited over the resultant structure and subsequently patterned in any suitable manner. Alternatively, the polymer 120 may be selectively deposited. A non-limiting example of a suitable polymer 120 is a polymerized silicone hydrogel, which may be deposited in its monomer form and subsequently cured in-situ to form a cross-linked matrix in which the fluorophores are embedded. A photodiode die 130 is subsequently flip-chipped and bonded to the pre-formed metal contacts 290 such that its photosensitive surface faces the polymer 120. The photodiode chip 130 typically also comprises the read-out electronics, e.g. an ASIC comprising a suitable transducer, which is connected to the coil or antenna 240 through the metal contact pads 290.

The die 130 is subsequently encapsulated in an insulating polymer 320, e.g. a flexible silicone hydrogel, after which the second transfer substrate 260 is released from the wafer, e.g. by exposure to UV radiation or a thermal budget. This is shown in step (m). The resultant device is subsequently placed in a mould 300 for forming the flexible insert such as an ophthalmic lens 100 in any suitable manner.

Suitable materials for the ophthalmic lens 100 or other flexible inserts that can be worn in the eye include polyvinyl alcohols such as PVP, HEMA (hydroxyl ethyl methacrylate), hydrogel, and silicone hydrogel. HEMA-type lenses are lenses consisting of a soft polymer, e.g. Halifilcon B, with a water content of 60%. The silicone-hydrogel lenses are soft polymers with a high oxygen permeability. The silicone hydrogel materials combine the benefits of silicone—which has extremely high oxygen permeability—with the comfort and clinical performance of the conventional hydrogels.

The water content of second generation silicone hydrogel lenses are higher due to the addition of hydrophilic ligands to the silicone back bone. In such second generation silicon hydrogels, a polar substituent is added without changing the structure (backbone) of the silicone hydrogel. Example tradenames of such second generation silicon hydrogels include Galyfilcon A and Senofilcon A.

In a third generation lens polymer wetting is improved due to the addition of other hydrophilic molecules to the silicone blend. For instance, if two siloxy macromers of different sizes are combined, very high oxygen permeability can be achieved for a given water content. Comfilcon A and Enfilcon A are trade name examples of such third generation silicone hydrogel polymers.

The insert 100 does not need to be extremely flexible. For instance, the insert 100 may be an ophthalmic lens with limited flexibility (a hard contact lens). Examples of materials for rigid lenses that can be used to manufacture such inserts 100 include acrylates polymerized from e.g. methyl acrylate, ethyl acrylate hydroxyethyl methacrylate, butyl acrylate, 2-ethyl hexyl acrylate, 2-chloroethyl vinyl ether, or terephtalates such as PET. These materials have typically a larger index of refraction than the soft silicon hydrogel based materials n=1.42-1.45 and n=1.37-1.42 respectively. The size of the insert however, should be kept relatively small in order to keep the advantages such as flexibility, water content, wetting, and oxygen permeability.

Embodiments of the flexible insert 100 are not limited to lenses only. An alternative embodiment is a fiber made from a transparent material with limited flexibility such as PMMA on which the LED is positioned. Such a fiber may be combined with a contact lens doped with the fluorophores 120, in which case during use the fiber end should be placed in the vicinity of the contact lens doped with the fluorophores. The die 130 including the photodetector should be integrated in the contact lens as previously explained. The orientation of the fiber should preferably be chosen to be perpendicular to the surface of the photodetector to maximize signal to noise ratios of the fluorescent light to be detected.

At this point it is noted that in the context of the present invention, a hydrogel is a porous crosslinked polymer matrix filled with water suitable for trapping small molecules such as the fluorophores of interest in the matrix. In general, small molecules such as dyes, biomolecules, and enzymes can be physically entrapped into a matrix material having pores smaller than the size of the entrapped molecules. Also chemical linkage of the fluorophore molecules to the matrix material is feasible. In physically entrapping gels, the fluorophore has to be added prior to the crosslinking of the gel. In such cases care has to be taken that the conditions used during polymerization do not damage the fluorophore.

It is further noted that any suitable method for manufacturing an ophthalmic lens 100 may be applied. Such lens manufacturing methods range from injection moulding to diamond turning to spin casting techniques. The most precise method is diamond turning where the lens is cut and polished on a CNC lathe. Material is removed using a diamond cutting tool starting from a cylindrical disk of pre-polymerized material until the final desired shape is obtained. A spin-cast lens is a lens manufactured by whirling liquid silicone in a revolving mold at high speed. Injection molding where the liquid monomer is injected into a mould under pressure and subsequently polymerized with computer control is a common method to create nearly perfectly shaped lenses.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An insert for placement on a human eye, comprising:
    a light source in said insert such that light emitted from the light source is shielded from the human eye upon correct placement of the insert on the human eye, the light source having a light path;
    a light-responsive material placed in the light path of the light source, said light-responsive material emitting light upon stimulation by the light emitted from said light source, wherein at least one of an intensity and a wavelength of said stimulated emission is proportional to a chemical interaction of the light-sensitive material with an analyte of interest;
    a photodetector that is configured to detect the light emitted by the light-responsive material; and
    a transmitter coupled to the photodetector that is configured to transmit a photodetector reading.

2. The insert of claim 1, further comprising:
    an optical fiber configured to guide collimated light from the light source to the light-responsive material.

3. The insert of claim 1, wherein the insert further comprises:
    a first flexible layer; and
    a second flexible layer, wherein the light source, the light-responsive material, the photodetector and the transmitter are located between said first and second flexible layers.

4. The insert of claim 1, wherein the photodetector comprises:
    a plurality of sensing elements that are configured to ratiometrically detect the emitted light.

5. The insert of claim 1, wherein at least one of a first reflective layer, a refractive layer, and an interface is present between the light source and the human eye to prevent light emitted by the light source from entering the human eye.

6. The insert of claim 5, wherein the light source is placed between the first reflective layer and a further reflective layer opposite the first reflective layer.

7. The insert of claim 1, wherein a light-sensitive surface of the photodetector is facing the human eye upon correct placement of the insert in the human eye.

8. The insert of claim 7, wherein the photodetector is placed adjacent to and in the proximity with the light source such that light coupled out of the light source substantially evades said light-sensitive surface.

9. The insert of claim 1, further comprising:
    a color filter placed over the photodetector that is configured to filter out the light emitted by the light source.

10. The insert of claim 1, further comprising:
    a charge storage element that is configured to power the light source, the photodetector, the transmitter, and an inductive coil or antenna in the perimeter of the insert, said inductive coil or antenna being coupled to the charge storage element and configured to recharge the charge storage element upon exposure to electromagnetic radiation.

11. The insert of claim 1, wherein the light source is a light emitting diode, the light emitting diode further comprising:
    a calibration circuit that is configured to measure a junction temperature of the light emitting diode and control at least one of a drive current and a forward voltage of said light emitting diode in response to said junction temperature measurement.

12. The insert of claim 1, wherein the analyte of interest is glucose.

13. The insert of claim 12, wherein the light-responsive material is a boronic acid according to Formula I:

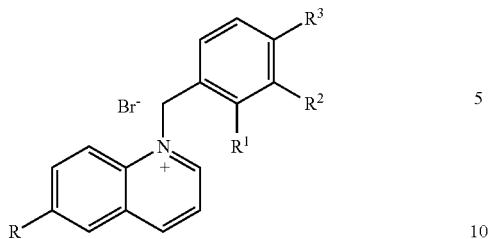

wherein R is selected from $CH_3$ and $OCH_3$, wherein at most one of $R_1$-$R_3$ is a B(OH)$_2$ group with the remaining groups being hydrogen.

14. A glucose-monitoring system comprising:
   the insert of claim 1; and
   a receive that is configured to receive a signal transmitted by the transmitter of the insert and translate a reading from the photodetector into a glucose level.

15. The glucose-monitoring system of claim 14, further comprising:
   a holder for the insert, said holder being configured to recharge an energy storage element of the insert.

16. The insert of claim 4, wherein each of the plurality of sensing elements is covered with a different color filter.

17. The insert of claim 1, further comprising:
   a clock configured to provide duty cycling for the insert.

18. The insert of claim 17, wherein the clock is a CMOS ring oscillator.

19. The insert of claim 1, wherein magnetic induction is used to continuously transfer power to the insert.

* * * * *